United States Patent
Fritzinger (10) Patent No.: US 10,251,654 B2
(45) Date of Patent: Apr. 9, 2019

(54) CUSTOMIZED PATIENT-SPECIFIC SURGICAL INSTRUMENT WITH METALLIC INSERT

(71) Applicant: DEPUY SYNTHES PRODUCTS, INC., Raynham, MA (US)

(72) Inventor: Daniel D. Fritzinger, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 273 days.

(21) Appl. No.: 15/394,893

(22) Filed: Dec. 30, 2016

(65) Prior Publication Data

US 2018/0185033 A1 Jul. 5, 2018

(51) Int. Cl.
| A61B 17/15 | (2006.01) |
| A61B 17/17 | (2006.01) |
| A61B 17/00 | (2006.01) |
| A61B 34/10 | (2016.01) |
| A61B 17/56 | (2006.01) |

(52) U.S. Cl.
CPC .......... *A61B 17/157* (2013.01); *A61B 17/154* (2013.01); *A61B 17/155* (2013.01); *A61B 17/1764* (2013.01); *A61B 2017/00526* (2013.01); *A61B 2017/568* (2013.01); *A61B 2034/108* (2016.02)

(58) Field of Classification Search
CPC .... A61B 17/157; A61B 17/154; A61B 17/155
See application file for complete search history.

(56) References Cited

U.S. PATENT DOCUMENTS

| 4,487,203 A * | 12/1984 | Androphy | A61B 17/154 |
| | | | 33/512 |
| 7,468,075 B2 | 12/2008 | Lang et al. | |
| 7,534,263 B2 | 5/2009 | Burdulis, Jr. et al. | |
| 7,615,054 B1 | 11/2009 | Bonutti | |
| 7,747,305 B2 | 6/2010 | Dean et al. | |
| 7,983,777 B2 | 7/2011 | Melton et al. | |
| 8,083,745 B2 | 12/2011 | Lang et al. | |
| 8,167,888 B2 | 5/2012 | Steffensmeier | |
| 8,234,097 B2 | 7/2012 | Steines et al. | |
| 8,257,360 B2 | 9/2012 | Richard et al. | |
| 8,377,066 B2 | 2/2013 | Katrana et al. | |
| 8,439,926 B2 | 5/2013 | Bojarski et al. | |
| 8,500,740 B2 | 8/2013 | Bojarski et al. | |
| 8,617,175 B2 | 12/2013 | Park et al. | |
| 8,623,026 B2 | 1/2014 | Wong et al. | |
| 9,675,471 B2 | 6/2017 | Bojarski et al. | |

(Continued)

FOREIGN PATENT DOCUMENTS

| CA | 2447694 A1 | 12/2002 |
| CA | 2696584 A1 | 2/2009 |

(Continued)

OTHER PUBLICATIONS

International Search Report and Written Opinion, International Application No. PCT/US2017/063624, dated Feb. 7, 2018, 6 pages.

*Primary Examiner* — Christian Sevilla (74) *Attorney, Agent, or Firm* — Barnes & Thornburg LLP (57) ABSTRACT

A surgical cutting guide including a customized, patient-specific contour is disclosed. The surgical cutting guide includes a metallic insert to guide a cutting tool in cutting a patient's bone.

20 Claims, 10 Drawing Sheets

(56) References Cited

U.S. PATENT DOCUMENTS

| | | | |
|---|---|---|---|
| 2002/0068979 A1* | 6/2002 | Brown | A61B 17/155 623/20.3 |
| 2003/0045883 A1* | 3/2003 | Chow | A61B 17/15 606/88 |
| 2003/0100907 A1* | 5/2003 | Rosa | A61B 17/155 606/86 R |
| 2009/0024131 A1 | 1/2009 | Metzger et al. | |
| 2009/0088753 A1 | 4/2009 | Aram et al. | |
| 2009/0131941 A1 | 5/2009 | Park et al. | |
| 2009/0222014 A1 | 9/2009 | Bojarski et al. | |
| 2010/0185202 A1 | 7/2010 | Lester et al. | |
| 2010/0212138 A1 | 8/2010 | Carroll et al. | |
| 2012/0041446 A1 | 2/2012 | Wong et al. | |
| 2012/0123422 A1 | 5/2012 | Agnihotri et al. | |
| 2012/0209394 A1 | 8/2012 | Bojarski et al. | |
| 2013/0296874 A1 | 11/2013 | Chao | |
| 2013/0317510 A1 | 11/2013 | Couture et al. | |
| 2015/0088143 A1 | 3/2015 | Lipman et al. | |
| 2015/0157341 A1 | 6/2015 | Catanzarite et al. | |
| 2017/0027587 A1 | 2/2017 | Fraone et al. | |

FOREIGN PATENT DOCUMENTS

| | | |
|---|---|---|
| CA | 2753485 A1 | 9/2010 |
| EP | 2649951 A2 | 10/2013 |
| EP | 3096693 A1 | 11/2016 |
| FR | 2918554 A1 | 1/2009 |
| WO | 2008157412 A2 | 12/2008 |
| WO | 2009111639 A1 | 9/2009 |
| WO | 2010121147 A1 | 10/2010 |
| WO | 2011106430 A1 | 9/2011 |
| WO | 2012024317 A2 | 2/2012 |

\* cited by examiner

CUSTOMIZED PATIENT-SPECIFIC SURGICAL INSTRUMENT WITH METALLIC INSERT

TECHNICAL FIELD

The present disclosure relates generally to orthopaedic surgical instruments and, more particularly, to surgical instruments used to resect a patient's bone.

BACKGROUND

Joint arthroplasty is a well-known surgical procedure by which a diseased and/or damaged natural joint is replaced by a prosthetic joint. Typical artificial joints include knee prostheses, hip prostheses, shoulder prostheses, ankle prostheses, and wrist prostheses, among others. To facilitate the replacement of the natural joint with the prosthesis, orthopaedic surgeons use a variety of orthopaedic surgical instruments such as, for example, saws, drills, reamers, rasps, broaches, cutting blocks, drill guides, milling guides, and other surgical instruments. Typically, the orthopaedic surgical instruments are generic with respect to the patient such that the same orthopaedic surgical instrument may be used on a number of different patients during similar orthopaedic surgical procedures.

In some surgical procedures, it is desirable to use surgical instruments that have been customized for use with a particular patient. Such "customized patient-specific orthopaedic surgical instruments" are surgical tools for use by a surgeon in performing an orthopaedic surgical procedure that is intended, and configured, for use on a particular patient. It should be appreciated that these instruments are distinct from standard, non-patient specific orthopaedic surgical instruments that are intended for use on a variety of different patients. These customized patient-specific orthopaedic surgical instruments are distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

SUMMARY

According to one aspect of the disclosure, an orthopaedic surgical instrument is disclosed. The orthopaedic surgical instrument is customized to a particular patient and includes a customized patient-specific contour defined therein that is configured to receive a portion of the patient's bone having a corresponding positive contour. The orthopaedic surgical instrument includes a metallic insert that defines a cutting guide sized and shaped to receive a cutting tool, such as, for example, a surgical saw or drill. The metallic insert is secured to a polymeric body of the orthopaedic surgical instrument via a snap feature that deflects during assembly without exceeding the yield strength of the polymeric material. The metallic insert also includes in some embodiments a key that is received in a keyway or slot defined in the polymeric body.

According to another aspect, the orthopaedic surgical instrument includes a body having a bone-facing first surface, a second surface, and a passageway. The bone-facing first surface has a customized patient-specific contour defined therein that is configured to receive a portion of a patient's bone having a corresponding positive contour. The second surface is positioned opposite the first surface. The passageway is positioned between a first opening in the first surface and a second opening defined in the second surface.

The orthopaedic surgical instrument also includes a metallic insert that is sized to be received in the passageway of the body. The insert includes an upper surface and a cutting guide slot. The upper surface extends from a first end facing the first opening of the body to a second end facing the second opening of the body. The cutting guide slot is aligned with the first and second openings and is sized to receive a surgical cutting blade. The upper surface is sloped such that the first end is positioned below the second end when the surgical cutting instrument is viewed in a cross-sectional plane. The body includes a retaining flange extending into the passageway between the second opening and the second end of the upper surface, the retaining flange having a tip positioned below the second end when the surgical cutting instrument is viewed in the cross-sectional plane.

In some embodiments, the tip of the retaining flange is positioned above the first end of the upper surface when the surgical cutting instrument is viewed in the cross-sectional plane. In some embodiments, the retaining flange includes a sloped bottom surface that extends from an edge connected to an inner surface of the body to the tip of the retaining flange.

In some embodiments, the upper surface of the metallic insert is a first upper surface, and the metallic insert includes a substantially planar second upper surface configured to face a substantially planar inner surface of the body.

In some embodiments, the metallic insert includes a recess that extends inwardly from the second upper surface to the first upper surface.

In some embodiments, the passageway includes (i) a first section extending from the first opening to an intermediate opening defined in a base surface of the body, and (ii) a second section extending from the intermediate opening to the second opening, the first section being more narrow than the second section when the surgical cutting instrument is viewed in the cross-sectional plane.

In some embodiments, the body includes a channel positioned below and opening into the passageway, and the metallic insert includes a key that is received in the channel.

In some embodiments, the metallic insert is offset inwardly from the bone-facing surface of the block. In some embodiments, the body is formed from a polymeric material. Additionally, in some embodiments, the customized patient-specific negative contour is configured to receive a portion of an anterior side of a patient's tibia that has a corresponding positive contour.

According to another aspect, a surgical cutting guide instrument includes a metallic insert. The metallic insert includes a upper surface and a cutting guide slot. The upper surface extends from a first end to a second end, and the cutting guide slot is sized to receive a surgical cutting blade. The upper surface includes a first surface that is a substantially planar surface and a second surface that is deflectable. A catch is positioned at the second end of the second surface.

In some embodiments, the second surface is sloped such that its first end is positioned below its second end when the surgical cutting guide is viewed in a cross-sectional plane. Additionally, in some embodiments, the metallic insert includes a recess that extends inwardly from the first upper surface to the second upper surface. In some embodiments, the metallic insert further includes at least one key extending from a bottom surface of the metallic insert opposite the upper surface.

In some embodiments, the insert includes a cantilevered body that includes the second surface and a plate that includes the first surface. The cantilevered body is coupled to the plate.

In some embodiments, the catch extends upwardly from the cantilevered body at the second end of the second surface. The catch is positioned inwardly relative to the second end of the second surface when the surgical cutting guide is viewed in a cross-sectional plane.

In some embodiments, the cantilevered body further includes a groove, the catch is positioned in the groove.

In some embodiments, the surgical cutting guide instrument further includes a body including a bone-facing first surface, a second surface, and a passageway. The bone-facing first surface has a customized patient-specific contour defined therein that is configured to receive a portion of a patient's bone having a corresponding positive contour. The second surface is positioned opposite the first surface. The passageway is positioned between a first opening in the first surface and a second opening defined in the second surface. The passageway has the metallic insert.

In some embodiments, the body includes a retaining flange extending into the passageway between the second opening and the second end of the upper surface. The retaining flange has a tip positioned below the catch when the surgical cutting guide is viewed in the cross-sectional plane.

According to another aspect, a method of assembling a surgical cutting block assembly having a body and a metallic insert is disclosed. The method comprises steps of: aligning the metallic insert with a passageway of the body, engaging a deflectable upper surface of the metallic insert into the passageway with a tip of a retaining flange of the body that extends into the passageway, advancing the metallic insert along the passageway such that the engagement of the deflectable upper surface of the metallic insert with the retaining flange of the body causes the upper surface to deflect inwardly, and disengaging the deflectable upper surface of the metallic insert from the retaining flange of the body such that the upper surface deflects outwardly and the tip of the retaining flange is positioned below the deflectable upper surface when the surgical cutting block is viewed in a cross-sectional plane.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopedics. Use of such anatomical reference terms in the specification and claims is intended to be consistent with their well-understood meanings unless noted otherwise.

Referring to FIGS. 1-6, one embodiment of an orthopaedic cutting guide 10 is shown. The orthopaedic cutting guide 10 is configured to be coupled to a bone, such as femur or tibia, of a patient. In some embodiments, the orthopaedic surgical cutting guide 10 may be customized to the particular patient based on the location at which the instrument is to be coupled to one or more bones of the patient, such as the femur and/or tibia. For example, in some embodiments, the customized patient-specific orthopaedic surgical cutting guide may include a bone-contacting or facing surface having a negative contour that matches or substantially matches the contour of a portion of the relevant bone of the patient. As such, the customized patient-specific orthopaedic surgical instrument is configured to be coupled to the bone of a patient in a unique location and position with respect to the patient's bone. That is, the negative contour of the bone-contacting surface is configured to receive the matching contour surface of the portion of the patient's bone. As such, the orthopaedic surgeon's guesswork and/or intraoperative decision-making with respect to the placement of the orthopaedic surgical instrument are reduced. For example, the orthopaedic surgeon may not be required to locate landmarks of the patient's bone to facilitate the placement of the orthopaedic surgical cutting guide, which typically requires some amount of estimation on part of the surgeon. Rather, the orthopaedic surgeon may simply couple the customized patient-specific orthopaedic surgical cutting guide on the bone or bones of the patient in the unique location. When so coupled, the cutting plane, drilling holes, milling holes, and/or other guides are defined in the proper location relative to the bone and intended orthopaedic prosthesis.

Figure 1:
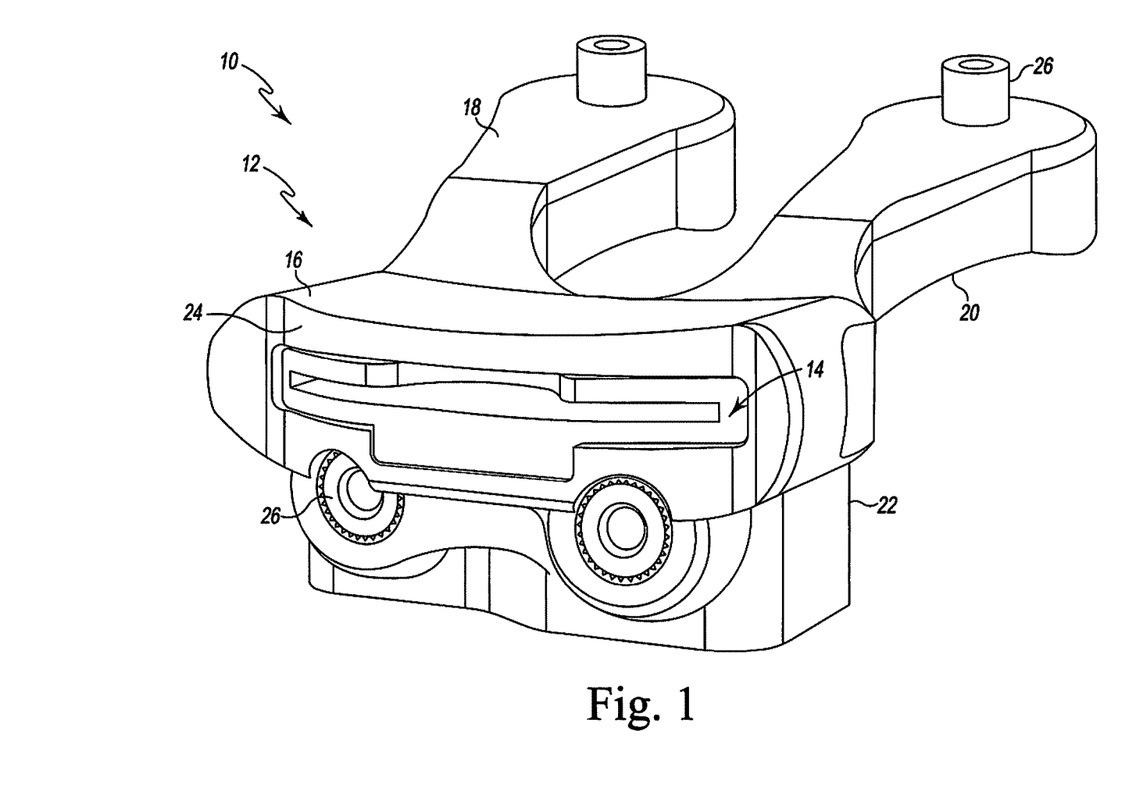
FIG. 1 is a perspective view of one embodiment of an orthopaedic cutting guide having a guide block and a guide insert.
Figure 6:
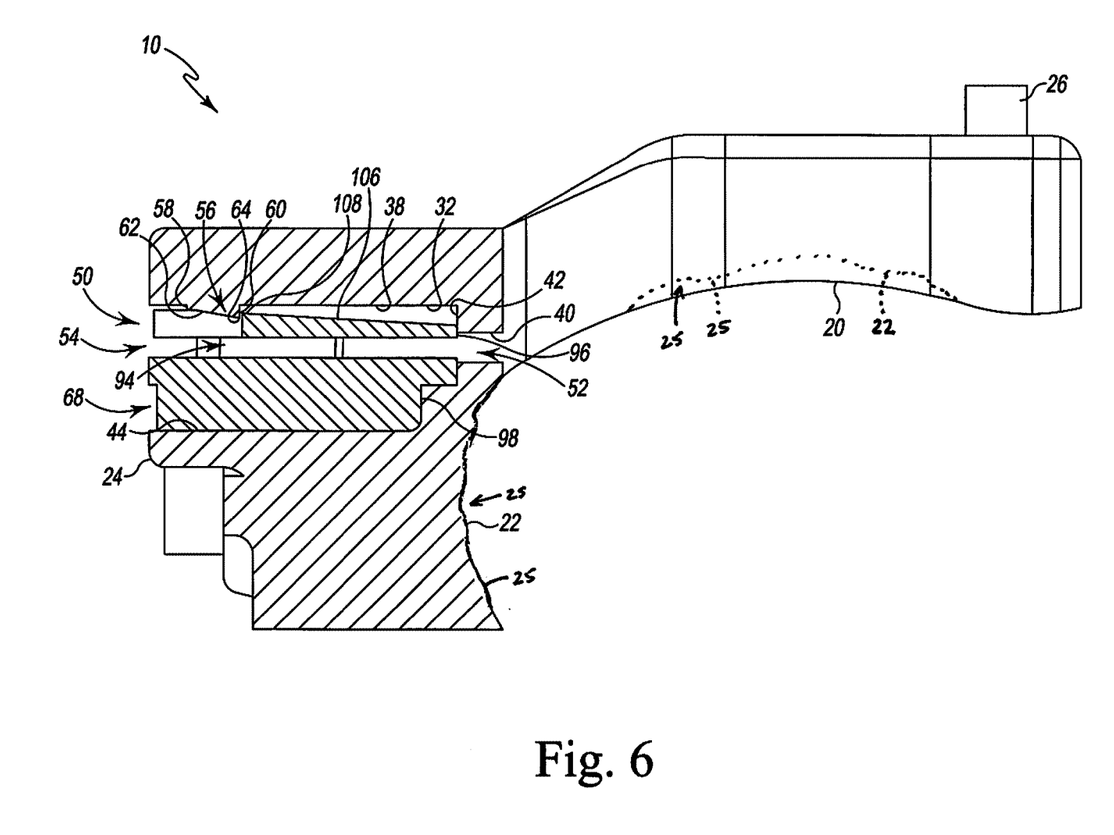
FIG. 6 is a cross-sectional view taken along the line 6-6 in FIG. 1.

The orthopaedic cutting guide 10 includes a guide block 12 and a guide insert 14. The guide block 12 includes a guide body 16 and two tabs 18. Two tabs 18 extend orthogonally from the guide body 16 and include bone-contacting or bone-facing surfaces 20 that are configured to wrap around condyles of the patient's bone. The guide body 16 includes a bone-contacting or bone-facing surface 22 and an outer surface 24 opposite the bone-facing surface 22. As shown in FIG. 6, the bone-facing surface 22 includes a plurality of negative contours, each of which is configured to receive a portion of the patient's bone having a corresponding contour. Each negative contour has a plurality of ridges and depressions 25 shaped to engage a corresponding plurality of ridges and depressions (not shown) in the portion of the patient's bone having a corresponding contour. The negative contour of the bone-facing surface 22 and the tabs 18 allow the positioning of the orthopaedic cutting guide 10 on the patient's bone. The guide block 12 further includes a number of pin guides 26. A pair of pin guides 26 is defined on the guide body 16, and another pair of pin guides 26 is defined on the tabs 18. In use, the pin guides 26 may be used as drill guides to establish guide pinholes in the bone of the patient for securing a number of guide pins (not shown) to the bone. The guide block 12 may then be coupled and secured to the patient's bone via the guide pins.

Additionally, the guide block 12 may be formed from polymeric materials such as, for example, polyamide, polyphenylsulfone, or polyketone. In such an embodiment, the surfaces used to guide surgical instruments, such pin guides for guiding drills and surgical pins, may be formed from a metallic material such as, for example, steel, titanium alloy, or cobalt chromium alloy. In addition, the guide insert 14 for guiding bone saws may be formed from a metallic material such as, for example, steel, titanium alloy, or cobalt chromium alloy. Such use of metallic components prevents the surgical tools from coming into contact with the polymeric materials of the guide block's body.

Figure 2:
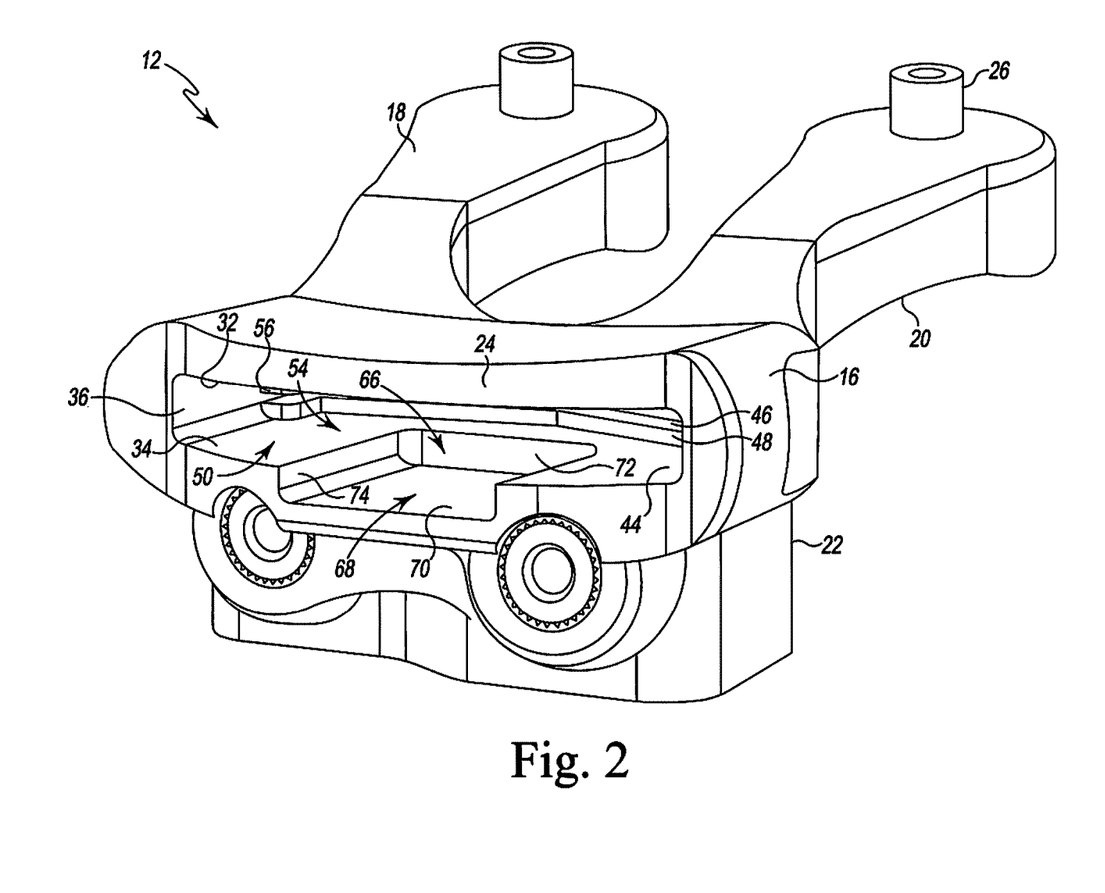
FIG. 2 is a perspective view of the guide block of the orthopaedic cutting guide of FIG. 1.

As shown in FIG. 2, the guide body 16 includes an upper wall 32, a lower wall 34 positioned opposite to the upper wall 32, and a pair of sidewalls 36 that connects the upper wall 32 and the lower wall 34. The guide body 16 further includes a passageway 54, which is sized to receive the metallic guide insert 14. The passageway 54 is defined between the upper wall 32 and the lower wall 34 and extends through the guide body 16 from the front opening 50 to the rear opening 52. The upper wall 32 further includes an upper surface 38, an upper rear surface 40, and an upper rear wall 42. The upper surface 38 and the upper rear surface 40 are generally planar and extend generally parallel to one another. The upper rear wall 42 extends downwardly from the upper surface 38 to the upper rear surface 40. Similarly, the lower wall 34 includes a lower surface 44, a lower rear surface 46, and a lower rear wall 48. The lower rear wall 48 extends upwardly from the lower surface 44 to the lower rear surface 46. Accordingly, a distance between the upper rear surface 40 and the lower rear surface 46 is shorter than a distance between the upper surface 38 and the lower surface 44.

Additionally, the upper surface 38, the lower surface 44, and the sidewalls 36 cooperate to define a front opening 50, which extends inwardly from the outer surface 24. The upper rear surface 40, the lower rear surface 46, and the sidewalls 36 cooperate to define a rear opening 52 that extends inwardly from the bone-facing surface 22. Because the distance between the upper rear surface 40 and the lower rear surface 46 is shorter than the distance between the upper surface 38 and the lower surface 44, the rear opening 52 has a smaller dimension in height than the front opening 50.

In the illustrative embodiment, the lower rear wall 48 extends laterally across the passageway 54 from one sidewall 36 to another sidewall 36. It should be appreciated that in some embodiments, the lower rear wall 48 may partially extend in the passageway 54 between the sidewalls 36. For example, the lower rear wall 48 may be positioned only at a center of the passageway 54 or on each side of the passageway 54.

The guide body 16 also includes a retaining flange 56, which is configured to engage the metallic guide insert 14 when the metallic guide insert 14 is received in the passageway 54. The retaining flange 56 extends downwardly from the upper surface 38 of the passageway 54 at the front opening 50. In the illustrative embodiment, the retaining flange 56 is wedge-shaped when viewed in a cross-sectional plane. The retaining flange 56 includes an outer edge 58, an inner edge 60, and a rectangular-shaped sloped surface 62 that extends from the outer edge 58 to the inner edge 60. The outer edge 58 and the inner edge 60 extend downwardly from the upper surface 38 of the passageway 54. The inner edge 60 has a length that is longer than a length of the outer edge 58 such that the sloped surface 62 has a downward slope from the outer edge 58 toward the inner edge 60. Additionally, the inner edge 60 has a tip 64 defined at the lowest point of the inner edge 60, and the tip 64 is positioned above the upper rear surface 40 of the upper wall 32 of the guide body 16.

Further, the lower surface 44 includes an opening 66 that extends downwardly from the lower surface 44 to define a channel 68. The channel 68 is generally rectangular-shaped and opens into the passageway 54. The channel 68 is further defined by a base surface 70 of the guide body 16, a rear wall 72, and a pair of sidewalls 74. The base surface 70 extends inwardly from the outer surface 24 of the guide body 16 to the rear wall 72. In that way, the base surface 70, the rear wall 72, and the pair of sidewalls 74 define a closed channel 68.

Figure 3:
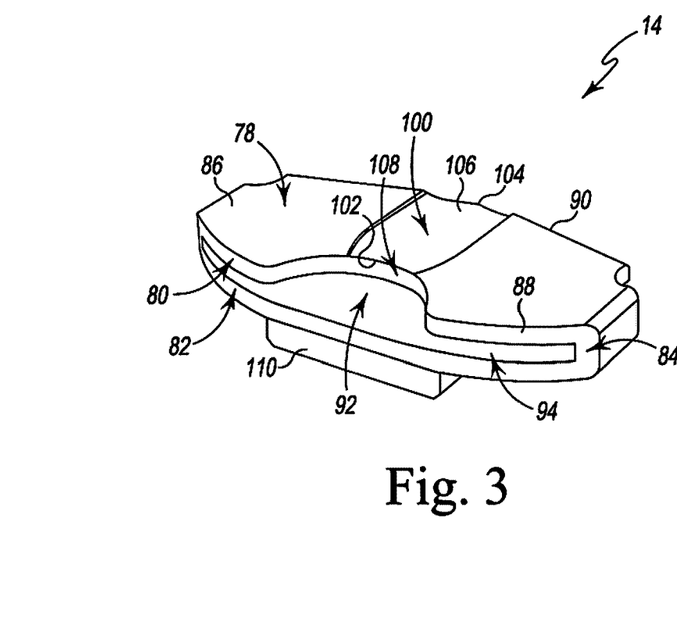
FIGS. 3-4 are perspective views of the guide insert of the orthopaedic cutting guide of FIG. 1.
Figure 4:
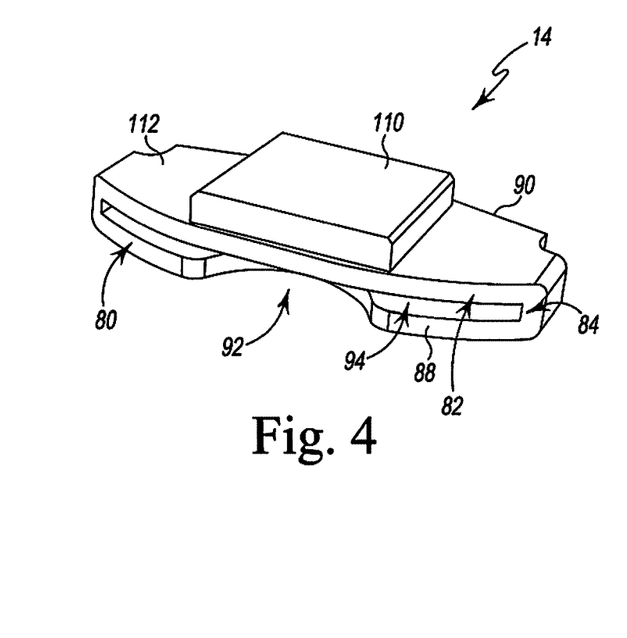

Referring now to FIGS. 3-4, the metallic guide insert 14 is shown. The metallic guide insert 14 includes an insert body 78 having an upper wall 80, a bottom wall 82, a pair of sidewalls 84 that connects the upper wall 80 and the bottom wall 82. The upper wall 80 has an upper surface 86, which is substantially planar and extends from a front surface 88 of the upper wall 80 to a rear surface 90 of the upper wall 80 opposite the front surface 88. The front surface 88 bows inwardly toward the rear surface 90 to define an opening 92. In the illustrative embodiment, the opening 92 is positioned at a center of the front surface 88. It should be appreciated that in some embodiments, the opening 92 may be positioned off-centered.

The insert body 78 further includes a cutting guide slot 94 between the upper wall 80 and the bottom wall 82. The cutting guide slot 94 extends from the front surface 88 to the rear surface 90. The cutting guide slot 94 is sized to receive a surgical cutting blade (not shown). In addition, the rear surface 90 includes an upper rear surface 96 and a lower rear surface 98 (see FIG. 6) spaced apart from the upper rear surface 96 by the cutting guide slot 94.

The insert body 78 includes a recess 100 defined in the upper surface 86 of the upper wall 80. The recess 100 has a base surface 106 that extends downwardly from the upper surface 86. The base surface 106 extends from a front edge 102 at the front surface 88 to a rear edge 104 at the rear surface 90. The base surface 106 further has a downward slope from the front edge 102 toward the rear edge 104 such that the front edge 102 is positioned above the rear edge 104 when viewed in a cross-sectional plane. In the illustrative embodiment, the front edge 102 is positioned at a central section the front surface 88, and the rear edge 104 is positioned at a central section of the rear surface 90. It should be appreciated that in some embodiments, the recess 100 and the opening 92 may be positioned off-centered. In other embodiments, the upper wall 80 may include a plurality of openings 92 and a plurality of recesses 100, each extending from the opening 92.

The insert body 78 further includes a catch 108. In the illustrative embodiment, the catch 108 is positioned at a most-inner point of the front surface 88 and is positioned above the rear edge 104 when viewed in a cross-sectional plane. The catch 108 is configured to engage the retaining flange 56 of the guide block 12.

Additionally, the upper wall 80 of the insert body 78 is deflectable such that when force is exerted on the base surface 106, the upper wall 80 deflects inwardly toward the bottom wall 82. When the force is relieved, the upper wall 80 deflects outwardly away from the bottom wall 82, which will be described in detail below.

The metallic guide insert 14 further includes a key 110 extending downwardly from a bottom surface 112 of the bottom wall 82. The bottom surface 112 is generally planar and is configured to engage the lower surface 44 of the guide body 16 within the passageway 54. The key 110 is generally rectangular-shaped and is sized and shaped to be received in the channel 68 of the passageway 54. In the illustrative embodiment, the key 110 is positioned at a center of the bottom surface 112 such that a center of the key 110 is vertically aligned with a center of the recess 100. It should be appreciated that in some embodiments, the key 110 may be positioned off-centered as will be described in detail below. In other embodiments, the metallic guide insert 14 may include more than one key, which will also be described in detail below.

Figure 5:
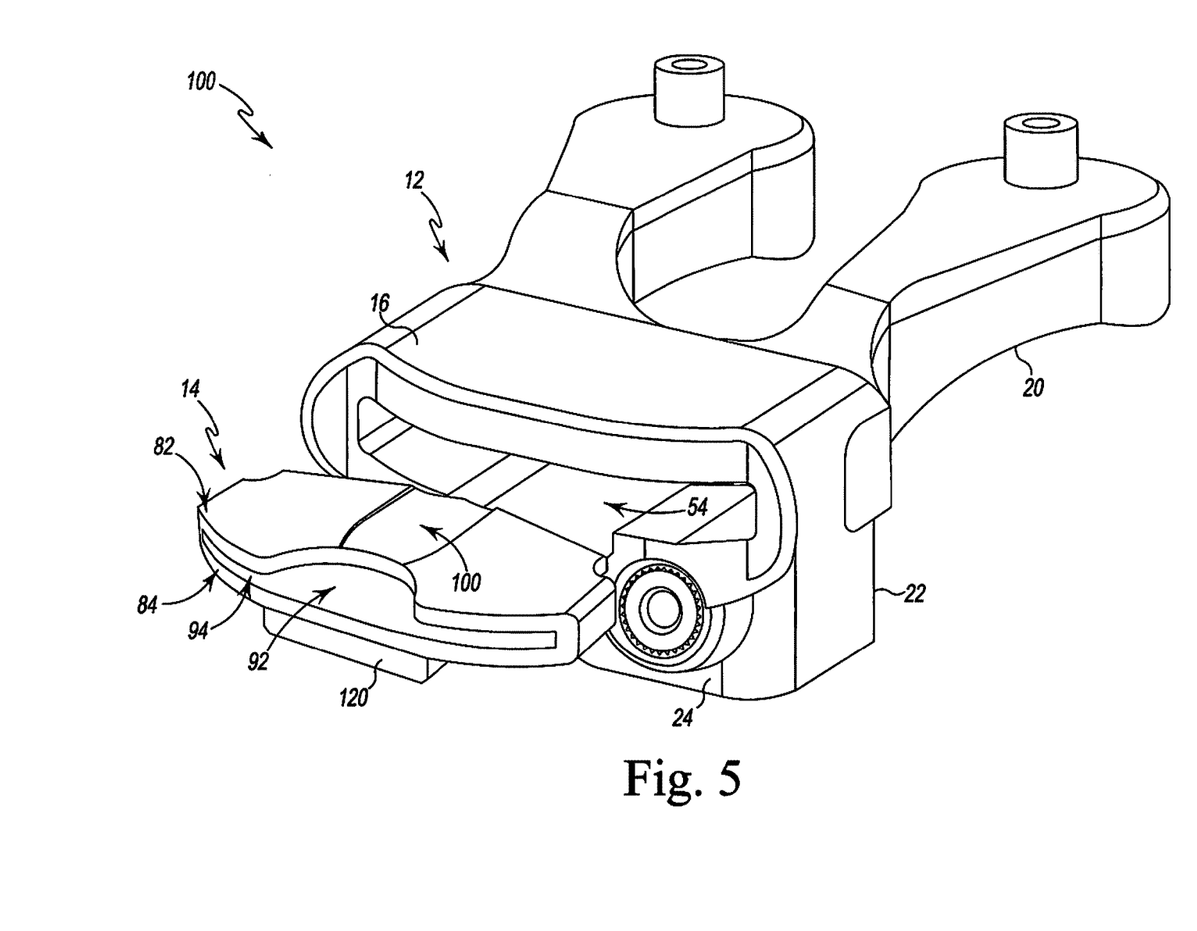
FIG. 5 is a partial exploded perspective view of the orthopaedic cutting guide of FIG. 1.

To assemble the orthopaedic cutting guide 10, a user aligns the metallic guide insert 14 with the passageway 54 of the guide block 12 as shown in FIG. 5. As described above, the passageway 54 is sized and shaped to receive the metallic guide insert 14, and the channel 68 of the guide block 12 is sized and shaped to receive the key 110 of the metallic guide insert 14. In addition, the tip 64 of the retaining flange 56 of the guide insert 14 is positioned above the rear edge 104 of the recess 100 when viewed in a cross-sectional plane. As the metallic guide insert 14 advances into the passageway 54, the retaining flange 56 passes the rear edge 104 and is positioned on the base surface 106. Specifically, the tip 64 of the retaining flange 56 touches and engages the base surface 106 of the recess 100. As described above, the base surface 106 has an upward slope in the direction the tip 64 is travelling along the base surface 106. Accordingly, as the tip 64 drags along the inclined base surface 106 toward the catch 108, the tip 64 exerts a downward force on the base surface 106 causing the base surface 106 to deflect inwardly toward the bottom wall 82.

When the metallic guide insert 14 is fully inserted into the passageway 54, the rear surface 90 faces the rear opening 52 and the front surface 88 faces the front opening 50 as shown in FIG. 6. In such configuration, the upper rear surface 96 of the rear surface 90 of the metallic guide insert 14 contacts the upper rear wall 42 of the guide body 16. Additionally, the lower rear surface 98 of the rear surface 90 contacts the rear wall 72 of the channel 68. The upper rear surface 96 and the lower rear surface 98 of the rear surface 90 cooperate to prevent the metallic guide insert 14 from further advancing into the passageway 54. At the same time, the retaining flange 56 disengages from the recess 100 and relieves the downward force from the base surface 106. The relief of force causes the base surface 106 to deflect outwardly away from the bottom wall 82. As shown in FIG. 6, the tip 64 of the retaining flange 56 is positioned below the catch 108 of the base surface 106 when viewed in a cross-sectional plane to secure the metallic guide insert 14 within the passageway 54. Moreover, the key 110 is completely received in the channel 68, and the rear surface 90 of the metallic guide insert 14 abuts the rear wall 72 of the channel 68.

Referring now to FIGS. 7-10, an orthopaedic cutting guide 200 is shown with another embodiment of a guide block 202 and a guide insert 204. Like the orthopaedic cutting guide 10, the guide block 202 may be formed from polymeric materials such as, for example, polyamide, polyphenylsulfone, or polyketone. In such an embodiment, the surfaces used to guide surgical instruments, such pin guides for guiding drills and surgical pins, may be formed from a metallic material such as, for example, steel, titanium alloy, or cobalt chromium alloy. In addition, the guide insert 204 for guiding bone saws may be formed from a metallic material such as, for example, steel, titanium alloy, or cobalt chromium alloy. Such use of metallic components prevents the surgical tools from coming into contact with the polymeric materials of the guide block's body.

Figure 7:
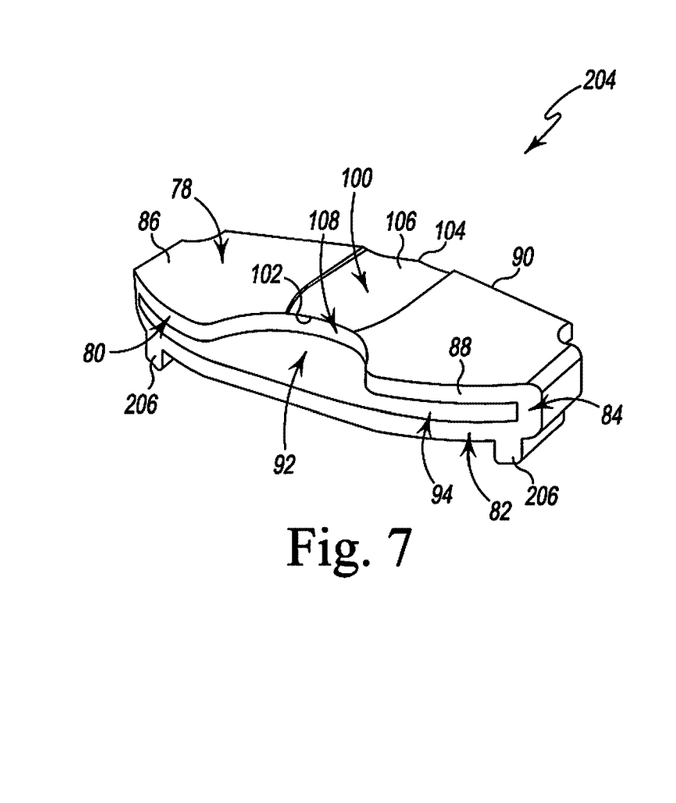
FIGS. 7-8 are perspective views of another embodiment of a guide insert of another embodiment of orthopaedic cutting guide.
Figure 8:
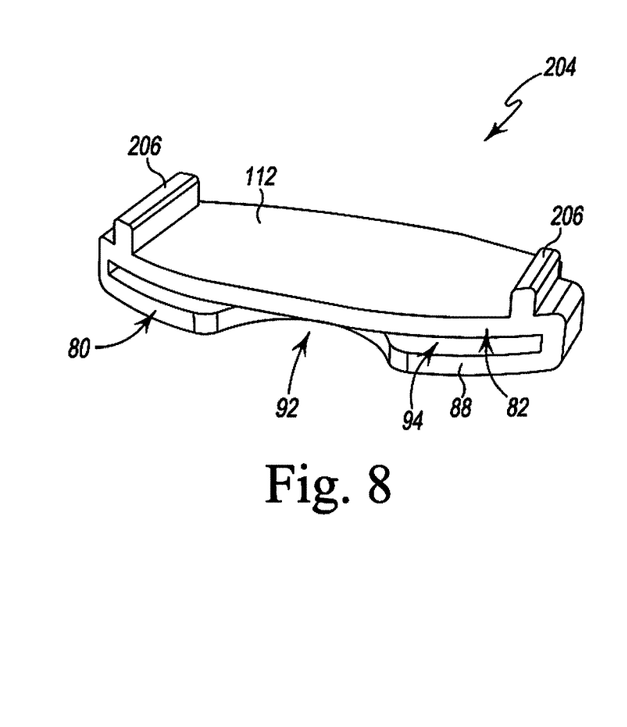

Referring now to FIGS. 7-8, the metallic guide insert 204 is shown. The metallic guide insert 204 shares many common features with the metallic guide insert 14, and the same reference numbers will be used to describe those common features. As described above, the metallic guide insert 204, like the metallic guide insert 14, includes an insert body 78 having an upper wall 80, a bottom wall 82, sidewalls 84, and a cutting guide slot 94 between the upper wall 80 and the bottom wall 82. In the illustrative embodiment, the metallic guide insert 14 further includes a pair of keys 206 extending downwardly from a bottom surface 112 of the bottom wall 82. Each key 206 is generally narrow elongated rectangular-shaped and extends downwardly from the bottom wall 82 near each sidewall 84 such that the pair of keys 206 is symmetrically positioned on the insert body 78.

Figure 9:
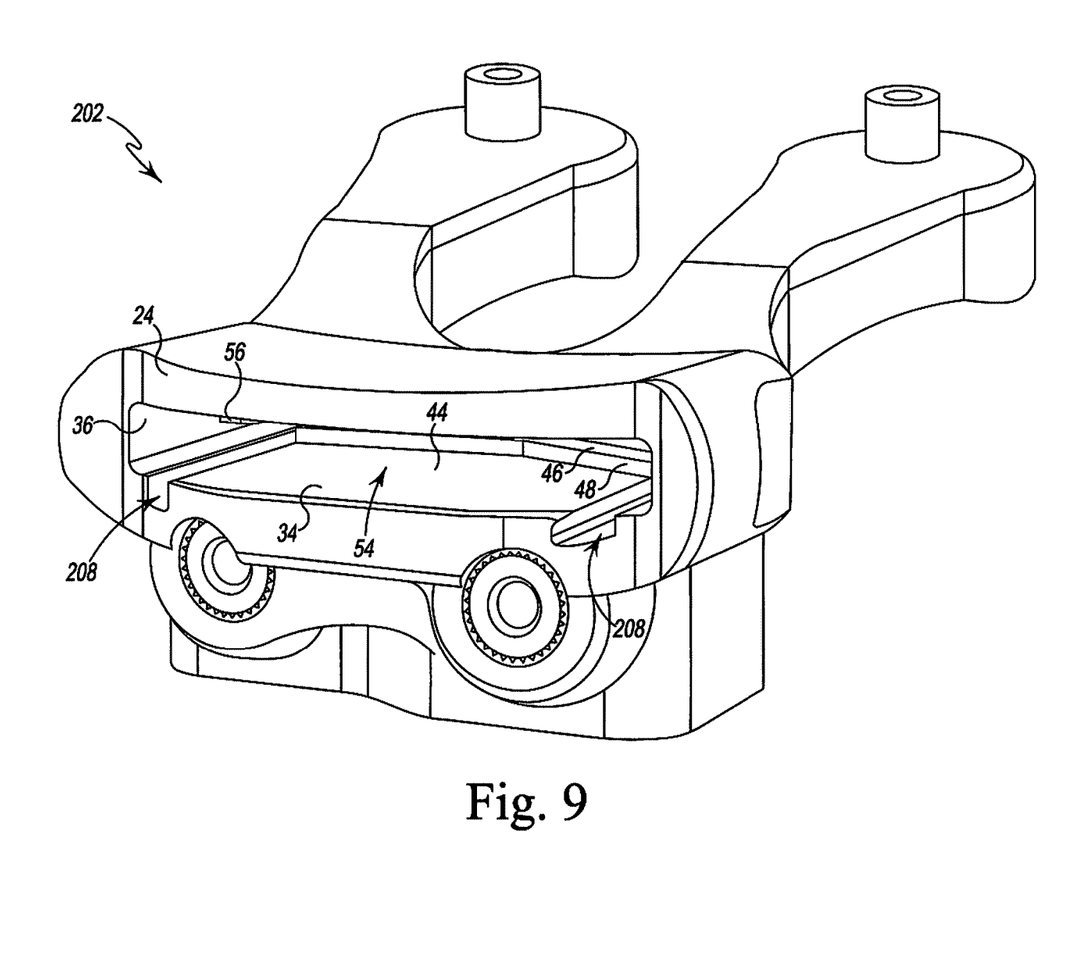
FIG. 9 is a perspective view of another embodiment of a guide block that is configured to receive the guide insert of FIGS. 7-8.
Figure 10:
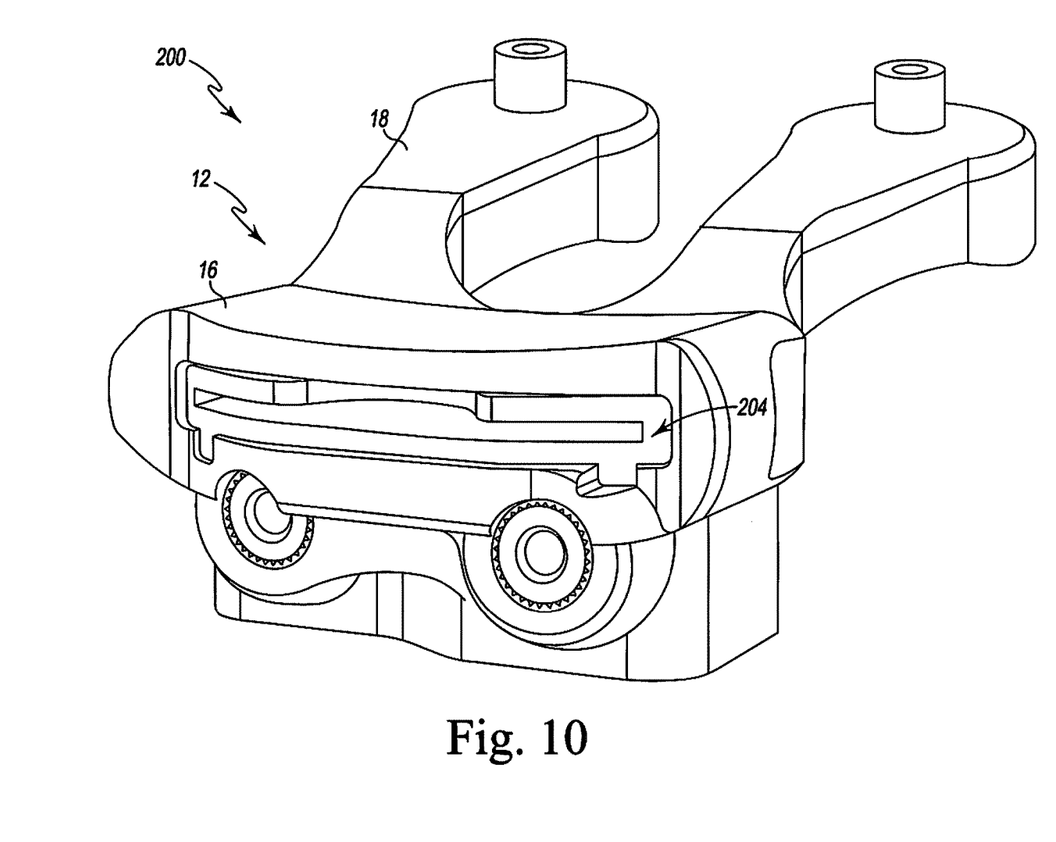
FIG. 10 is a perspective view of the orthopaedic cutting guide having the guide block of FIG. 9 and the guide insert of FIGS. 7-8.

Referring now to FIG. 9, the guide block 202 is shown. The guide block 202 shares many common features with the guide block 12, and the same reference numbers will be used to describe those common features. As described above, the guide block 202, like the guide block 12, includes a guide body 16 that includes an upper wall 32, a lower wall 34, and a passageway 54. The passageway 54 extends between the upper wall 32 and the lower wall 34 from the outer surface 24 to the bone-facing surface 22. As described above, the lower wall 34 includes a lower surface 44, a lower rear surface 46, and a lower rear wall 48. The lower rear wall 48 extends upwardly from the lower surface 44 to the lower rear surface 46. The guide block 202 further includes a pair of channels 208 that extends downwardly from the lower surface 44. In the illustrative embodiment, the channels 208 are symmetrically positioned in the passageway 54 and are sized and shaped to receive the keys 206. Each channel 208 is generally narrow elongated rectangular-shaped and is defined by a base surface 70 of the guide body 16, a rear wall 72, and a pair of sidewalls 74. The base surface 70 extends inwardly from the outer surface 24 of the guide body 16 to the rear wall 72. As described above, when the orthopaedic cutting guide 200 is assembled, as shown in FIG. 10, the passageway 54 of the guide block 202 receives the metallic guide insert 204, and each channel 68 of the guide block 202 is sized and shaped to receive each key 206 of the metallic guide insert 204.

Figure 11:
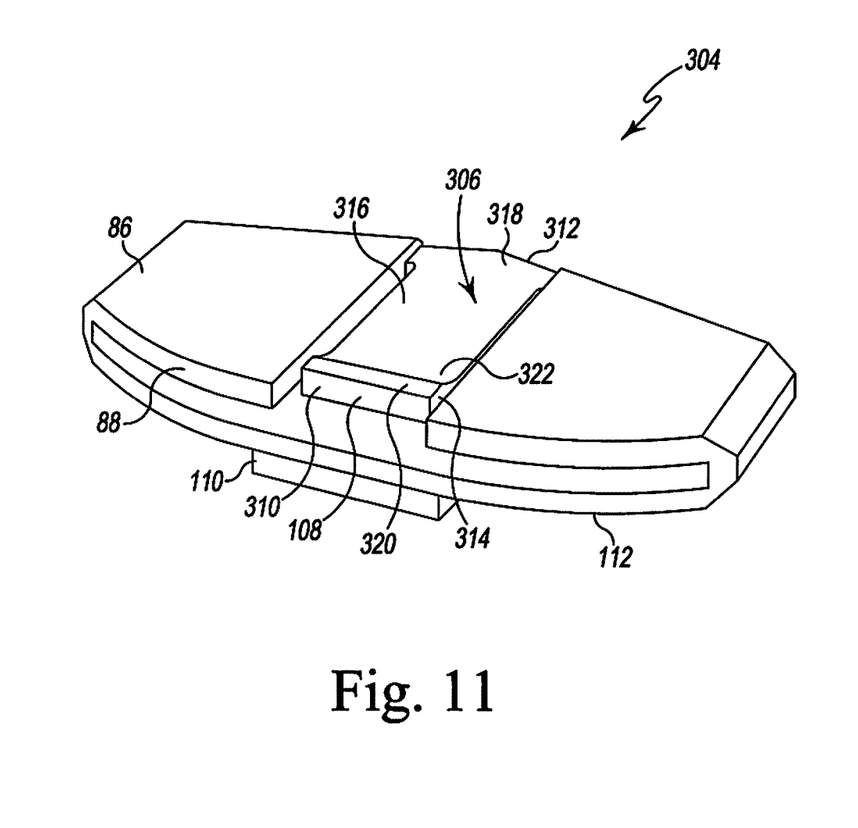
FIG. 11 is a perspective view of another embodiment of a guide insert.

Referring now to FIG. 11, alternative embodiment of a guide insert 304 configured for use with the guide block 12 of FIG. 2 is shown. The metallic guide insert 304 shares many common features with the metallic guide insert 14, and the same reference numbers will be used to describe those common features. As described above, the metallic guide insert 304, like the metallic guide insert 14, includes an insert body 78 that further includes an upper wall 80, a bottom wall 82, sidewalls 84, and a cutting guide slot 94 between the upper wall 80 and the bottom wall 82. The upper wall 80 has an upper surface 86, which is substantially planar and extends from a front surface 88 of the upper wall 80 to a rear surface 90 of the upper wall 80 opposite the front surface 88.

The metallic guide insert 304 includes a cantilevered body 306 defined at a center of the upper wall 80 and is deflectable relative to the upper surface 86 of the upper wall 80. The cantilevered body 306 includes a front surface 310, a rear surface 312 opposite the front surface 310, side surfaces 314, and a base surface 316 that extends from the rear surface 312 to the front surface 310. The cantilevered body 306 is coupled to the upper wall 80 at the rear surface 312 such that the rear surface 312 aligns with the rear surface 90 of the upper wall 80. The base surface 316 further includes a planar surface 318, a top surface 320, and a ramp surface 322 connecting the planar surface 318 and the top surface 320. The ramp surface 322 has an upward slope from the planar surface 318 to the top surface 320. The insert body 78 of the metallic guide insert 304 further includes a catch 108. In the illustrative embodiment, the catch 108 is defined at the front surface 310. It should be appreciated that in some embodiments, the whole base surface 316 may be sloped from the top surface 320 to the rear surface 312.

The metallic guide insert 304 further includes a key 110 extending downwardly from the bottom wall 82. The key 110 is generally rectangular-shaped and is sized and shaped to be received in the channel 68 of the passageway 54 of the guide block 12. In the illustrative embodiment, the key 110 is positioned at a center of the bottom wall 82 such that a center of the key 110 is vertically aligned with a center of the cantilevered body 306. It should be appreciated that in some embodiments, the key 110 may be positioned off-centered, or the metallic guide insert 14 may include more than one key.

When the metallic guide insert 304 is inserted in the guide block 12, the retaining flange 56 engages the cantilevered body 306. Specifically, a tip 64 of the retaining flange 56 touches and engages the base surface 316 of the cantilevered body 306. As the tip 64 drags along the inclined ramp surface 322 of the base surface 316 toward the catch 108, the tip 64 exerts the downward force on the base surface 316 causing the base surface 316 and the side surfaces 314 of the cantilevered body 306 to deflect inwardly relative to the upper wall 80.

When the metallic guide insert 14 is fully inserted into the passageway 54 of the guide block 12, the retaining flange 56 disengages from the cantilevered body 306 and relieves the downward force from the base surface 316. The relief of force causes the base surface 316 to deflect outwardly away from the bottom wall 82. Accordingly, similar to the orthopaedic cutting block 10 shown in FIG. 6, the tip 64 of the retaining flange 56 is positioned below the catch 108 of the base surface 316 when viewed in a cross-sectional plane to secure the metallic guide insert 14 within the passageway 54. Moreover, the key 110 is completely received in the channel 68, and the rear surface 90 of the metallic guide insert 14 abuts the rear wall 72 of the channel 68. However, it should be appreciated that in some embodiments, the metallic guide insert 304 may not include a key 110. In such embodiment, a corresponding guide block may not include a channel that is configured to receive the key.

Figure 12:
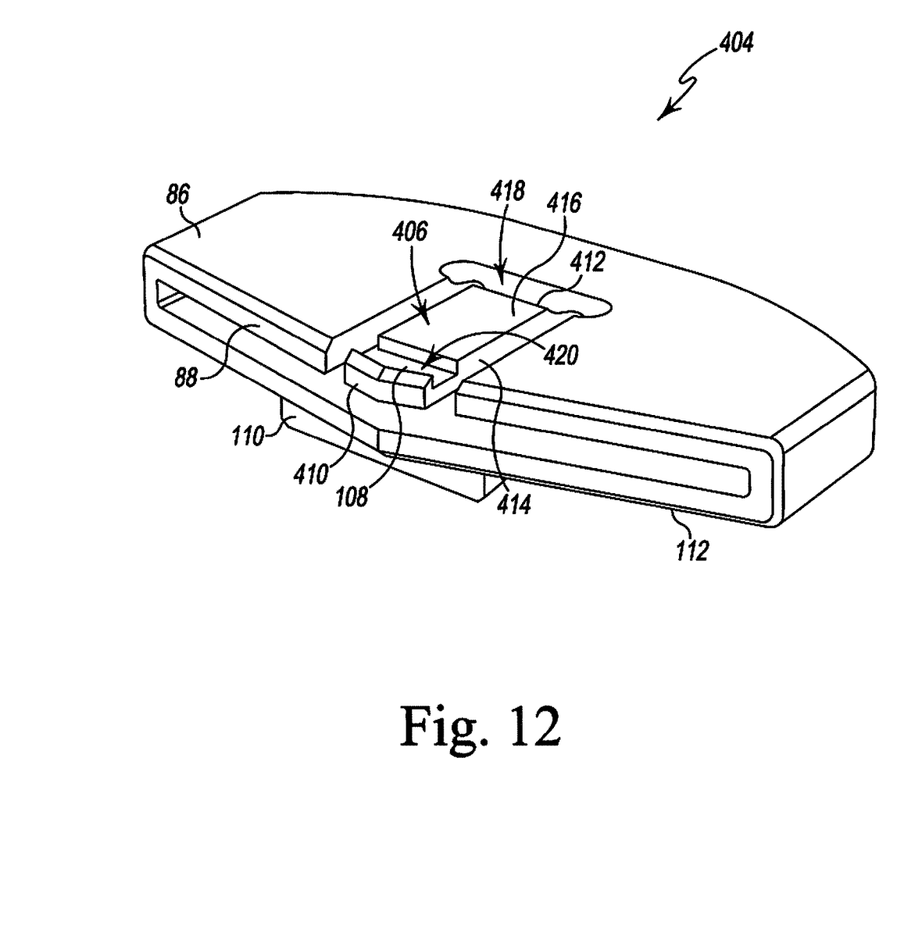
FIG. 12 is a perspective view of other embodiment of a guide insert.

Referring now to FIG. 12, another alternative embodiment of a guide insert 404 configured for use with the guide block 12 of FIG. 2 is shown. The metallic guide insert 404 shares many common features with the metallic guide insert 304 and the metallic guide insert 14, and the same reference numbers will be used to describe those common features. As described above, the metallic guide insert 404 includes an insert body 78 having an upper wall 80, a bottom wall 82, sidewalls 84, and a cutting guide slot 94 between the upper wall 80 and the bottom wall 82. The upper wall 80 has an upper surface 86, which is substantially planar and extends from a front surface 88 of the upper wall 80 to a rear surface 90 of the upper wall 80 opposite the front surface 88.

As described above, the metallic guide insert 404, like the metallic guide insert 304, includes a cantilevered body 406 defined at a center of the upper wall 80 and is deflectable relative to the upper surface 86 of the upper wall 80. The cantilevered body 406 includes a front surface 410, a rear surface 412 opposite the front surface 410, side surfaces 414, and a base surface 416 that extends from the rear surface 412 to the front surface 410. However, unlike the metallic guide insert 304, the upper surface 86 of the upper wall 80 includes a joint 418 that is connected to the rear surface 412 of the cantilevered body 406. The cantilevered body 406 further includes a groove 420 extending downwardly from the base surface 416 at the front surface 410. The insert body 78 of the metallic guide insert 404 further includes a catch 108. In the illustrative embodiment, the catch 108 is defined in the groove 420 and is configured to engage the retaining flange 56 of the guide block 12.

The metallic guide insert 404 further includes a key 110 extending downwardly from the bottom wall 82. The key 110 is generally rectangular-shaped and is sized and shaped to be received in the channel 68 of the passageway 54 of the guide block 12. In the illustrative embodiment, the key 110 is positioned at a center of the bottom wall 82 such that a center of the key 110 is vertically aligned with a center of the cantilevered body 406. It should be appreciated that in some embodiments, the key 110 may be positioned off-centered, or the metallic guide insert 14 may include more than one key.

When the metallic guide insert 404 is inserted in the guide block 12, a retaining flange 56 engages the cantilevered body 406. Specifically, a tip 64 of the retaining flange 56 touches and engages the base surface 416 of the cantilevered body 406. As the tip 64 drags along the inclined base surface 416 toward the catch 108, the tip 64 exerts the downward force on the base surface 416 causing the base surface 416 and the side surfaces 414 of the cantilevered body 406 to deflect inwardly relative to the upper wall 80.

When the metallic guide insert 14 is fully inserted into the passageway 54 of the guide block 12, the retaining flange 56 is positioned in the catch 108 to secure the metallic guide insert 14 within the passageway 54 and relieves the downward force from the base surface 416. The relief of force causes the base surface 416 to deflect outwardly away from the bottom wall 82. Moreover, the key 110 is completely received in the channel 68, and the rear surface 90 of the metallic guide insert 14 abuts the rear wall 72 of the channel 68. However, it should be appreciated that in some embodiments, the metallic guide insert 304 may not include a key 110. In such embodiment, a corresponding guide block may not include a channel that is configured to receive the key.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A surgical cutting guide instrument, comprising:
a body including (i) a bone-facing first surface having a customized patient-specific contour defined therein that is configured to receive a portion of a patient's bone having a corresponding positive contour, (ii) a second surface positioned opposite the first surface, and (iii) a passageway positioned between a first opening in the first surface and a second opening defined in the second surface, and
a metallic insert sized to be received in the passageway of the body, the insert including (i) an upper surface extending from a first end facing the first opening of the body to a second end facing the second opening of the body, and (ii) a cutting guide slot that is aligned with the first and second openings and is sized to receive a surgical cutting blade,
wherein the upper surface is sloped such that the first end is positioned below the second end when the surgical cutting instrument is viewed in a cross-sectional plane, and
wherein the body includes a retaining flange extending into the passageway between the second opening and the second end of the upper surface, the retaining flange having a tip positioned below the second end when the surgical cutting instrument is viewed in the cross-sectional plane.

2. The surgical cutting guide instrument of claim 1, wherein the tip of the retaining flange is positioned above the first end of the upper surface when the surgical cutting instrument is viewed in the cross-sectional plane.

3. The surgical cutting guide instrument of claim 1, wherein the retaining flange includes a sloped bottom surface that extends from an edge connected to an inner surface of the body to the tip of the retaining flange.

4. The surgical cutting guide instrument of claim 1, wherein the upper surface of the metallic insert is a first upper surface, and the metallic insert includes a substantially planar second upper surface configured to face a substantially planar inner surface of the body.

5. The surgical cutting guide instrument of claim 4, wherein the metallic insert includes a recess that extends inwardly from the second upper surface to the first upper surface.

6. The surgical cutting guide instrument of claim 1, wherein the passageway includes (i) a first section extending from the first opening to an intermediate opening defined in a base surface of the body, and (ii) a second section extending from the intermediate opening to the second opening, the first section being more narrow than the second section when the surgical cutting instrument is viewed in the cross-sectional plane.

7. The surgical cutting guide instrument of claim 1, wherein:
the body includes a channel positioned below and opening into the passageway, and
the metallic insert includes a key that is received in the channel.

8. The surgical cutting guide instrument of claim 1, wherein the metallic insert is offset inwardly from the bone-facing surface of the block.

9. The surgical cutting guide instrument of claim 1, wherein the body is formed from a polymeric material.

10. The surgical cutting guide instrument of claim 1, wherein the customized patient-specific negative contour is configured to receive a portion of an anterior side of a patient's tibia that has a corresponding positive contour.

11. A surgical cutting guide instrument, comprising a metallic insert including (i) a upper surface extending from a first end to a second end, and (ii) a cutting guide slot that is sized to receive a surgical cutting blade,
wherein the upper surface includes a first surface that is a substantially planar surface and a second surface that is deflectable, and
wherein a catch is positioned at the second end of the second surface.

12. The surgical cutting guide instrument of claim 11, wherein the second surface is sloped such that its first end is positioned below its second end when the surgical cutting guide is viewed in a cross-sectional plane.

13. The surgical cutting guide instrument of claim 11, wherein the metallic insert includes a recess that extends inwardly from the first upper surface to the second upper surface.

14. The surgical cutting guide instrument of claim 11, wherein the metallic insert further includes at least one key extending from a bottom surface of the metallic insert opposite the upper surface.

15. The surgical cutting guide instrument of claim 11, wherein the insert includes a cantilevered body that includes the second surface and a plate that includes the first surface, the cantilevered body is coupled to the plate.

16. The surgical cutting guide instrument of claim 15, wherein the catch extends upwardly from the cantilevered body at the second end of the second surface, wherein the catch is positioned inwardly relative to the second end of the second surface when the surgical cutting guide is viewed in a cross-sectional plane.

17. The surgical cutting guide instrument of claim 15, wherein the cantilevered body further includes a groove, the catch is positioned in the groove.

18. The surgical cutting guide instrument of claim 11 further comprising a body including (i) a bone-facing first surface having a customized patient-specific contour defined therein that is configured to receive a portion of a patient's bone having a corresponding positive contour, (ii) a second surface positioned opposite the first surface, and (iii) a passageway positioned between a first opening in the first surface and a second opening defined in the second surface, the passageway having the metallic insert.

19. The surgical cutting guide instrument of claim 18, wherein the body includes a retaining flange extending into the passageway between the second opening and the second end of the upper surface, the retaining flange has a tip positioned below the catch when the surgical cutting guide is viewed in the cross-sectional plane.

20. A method of assembling a surgical cutting block assembly having a body and a metallic insert, the method comprising steps of:

aligning the metallic insert with a passageway of the body,
engaging a deflectable upper surface of the metallic insert into the passageway with a tip of a retaining flange of the body that extends into the passageway,
advancing the metallic insert along the passageway such that the engagement of the deflectable upper surface of the metallic insert with the retaining flange of the body causes the upper surface to deflect inwardly, and
disengaging the deflectable upper surface of the metallic insert from the retaining flange of the body such that the upper surface deflects outwardly and the tip of the retaining flange is positioned below the deflectable upper surface when the surgical cutting block is viewed in a cross-sectional plane.

* * * * *